(12) United States Patent
Yablon (10) Patent No.: US 10,168,139 B2
(45) Date of Patent: *Jan. 1, 2019

(54) PARAMETER MEASUREMENT OF PHASE OBJECTS USING TOMOGRAPHIC IMAGING

(71) Applicant: Interfiber Analysis, LLC, Sharon, MA (US)

(72) Inventor: Andrew D. Yablon, Livingston, NJ (US)

(73) Assignee: Interfiber Analysis, LLC, Sharon, MA (US)

(*) Notice: Subject to any disclaimer, the term of this patent is extended or adjusted under 35 U.S.C. 154(b) by 1 day.

This patent is subject to a terminal disclaimer.

(21) Appl. No.: 15/182,969

(22) Filed: Jun. 15, 2016

(65) Prior Publication Data

US 2016/0298952 A1    Oct. 13, 2016

Related U.S. Application Data

(63) Continuation of application No. 13/916,515, filed on Jun. 12, 2013, now Pat. No. 9,395,267.

(51) Int. Cl.
| | |
|---|---|
| *G01B 9/04* | (2006.01) |
| *G01B 9/02* | (2006.01) |
| *G01M 11/00* | (2006.01) |
| *G01J 3/28* | (2006.01) |
| *A61B 5/00* | (2006.01) |

(Continued)

(52) U.S. Cl.
CPC ........ *G01B 9/02044* (2013.01); *A61B 5/0066* (2013.01); *G01B 9/04* (2013.01); *G01J 3/28* (2013.01); *G01M 11/37* (2013.01); *G01N 21/412* (2013.01); *G01N 21/45* (2013.01); *G01N 21/4795* (2013.01); *G01N 33/483* (2013.01); *G01N 33/4833* (2013.01); *G01N 2021/458* (2013.01)

(58) Field of Classification Search
CPC ......... G01J 3/28; G01M 11/37; A61B 5/0066; G01N 33/483; G01N 21/4795
See application file for complete search history.

(56) References Cited

U.S. PATENT DOCUMENTS

| | | |
|---|---|---|
| 7,352,474 B2 | 4/2008 | Bachim et al. |
| 8,405,836 B2 | 3/2013 | Yablon |

(Continued)

OTHER PUBLICATIONS

Abe, et al, "Photoelastic computer tomography: a novel measurement method for axial residual stress profile in optical fibers," J. Opt. Soc. Am. A., vol. 3, No. 1, Jan. 1986, pp. 133-138.

(Continued)

*Primary Examiner* — Hwa Lee
(74) *Attorney, Agent, or Firm* — Berkeley Law & Technology Group, LLP (57) ABSTRACT

Briefly, embodiments of methods and/or systems for tomographic imaging are disclosed. In an example embodiment, optical measurements may be obtained for at least a portion of an illuminated object at a plurality of focal positions between the illuminated object and an imaging lens and at a plurality of angular orientations. Rotated representations of the optical measurements may be projected onto a coordinate plane in which in-focus and out-of-focus rotated representations of the optical measurements may form a cross-sectional image of the illuminated portion of the object.

24 Claims, 6 Drawing Sheets

(51) Int. Cl.
G01N 21/47 (2006.01)
G01N 33/483 (2006.01)
G01N 21/41 (2006.01)
G01N 21/45 (2006.01)

(56) References Cited

U.S. PATENT DOCUMENTS

8,860,934 B2  10/2014  Yablon
8,867,028 B2  10/2014  Yablon
2005/0185192 A1  8/2005  Kim et al.

OTHER PUBLICATIONS

Bachim, et al, "Microinterferometric optical phase tomography for measuring small, asymmetric refractive-index differences in the profiles of optical fibers and fiber devices," Applied Optics, vol. 44, No. 3, Jan. 20, 2005, pp. 316-327.
Bachim, et al, "Refractive-index profiling of azimuthally asymmetric optical fibers by microinterferometric optical phase tomography," Optics Letters, vol. 30, No. 10, May 15, 2005, pp. 1126-1128.
Barty, et al, "Quantitative phase tomography," Optics Communications 175, Mar. 1, 2000, pp. 329-336.
Dragomir, et al, "Non-Destructive Three-Dimensional Index Profiling of Optical Fibres and Photonic Devices," ACOFT/AOS Proceedings, Melbourne, Australia, Jul. 10-13, 2006, pp. 103-105.
Dragomir, et al, "Three-Dimensional Quantitative Phase Imaging: Current and Future Perspectives," SPIE, vol. 6861, 2008, pp. 686106-1-686106-11.
Dragomir, et al, "Three-Dimensional Refractive Index Reconstruction With Quantitative Phase Tomography," Microscopy Research and Technique DOI10.1002/jemt, 2008, 6 Pages.
Gorski, "The influence of diffraction in microinterferometry and microtomography of optical fibers," Optics and Lasers in Engineering 41, 2004, pp. 565-583.
Gorski, et al, "Tomographic imaging of photonic crystal fibers," Optics Letters, vol. 32, No. 14, Jul. 15, 2007, pp. 1977-1979.
Gorski, et al, "Three-dimensional reconstruction of refractive index inhomogeneities in optical phase elements," Optics and Lasers in Engineering 38, 2002, pp. 373-385.
Jenkins, et al, "3D Characterization of the Refractive-Index and Residual-Stress Distributions in Optical Fibers," FiO/ LS Technical Digest, 2012, 2 Pages.
Kirchhof, et al, "Spatial Distribution Effects and Laser Efficiency in Er/Yb Doped Fibers," SPIE, vol. 5350, Bellingham, WA, 2004. pp. 222-233.
Kniazewski, et al, "Inspection of axial stress and refractive index distribution in polarization-maintaining fiber with tomographic methods," Optics and Lasers in Engineering 47, 2009, pp. 259-263.
Krajewski, et al, "Design, modeling, and prototyping of microinterferometric tomography system for optical fiber inspection," SPIE, vol. 6188, 2006, pp. 61880J-1-61880J-10.
Unger, et al, "Codoped Materials for High Power Fiber Lasers—Diffusion Behaviour and Optical Properties," SPIE, vol. 6469, Downloaded Dec. 17, 2010, pp. 646913-1-646913-12.
Yablon, "Measuring the Spatial Distribution of Rare-Earth Dopants in High-Power Optical Fibers," SPIE, vol. 7914, 2011, pp. 79141N-1-79141N-8.
Yablon, "New Transverse Techniques for Characterizing High-Power Optical Fibers," Optical Engineering, vol. 50(11), Nov. 2011, pp. 111603-1-111603-6.
U.S. Appl. No. 13/916,515, filed Jun. 12, 2013, 67 pages.
U.S. Appl. No. 13/916,515: Applicant Response to Pre-exam Formalities Notice, dated Sep. 4, 2014, 98 pages.
U.S. Appl. No. 13/916,515, filed Sep. 12, 2013, 3 pages.
U.S. Appl. No. 13/916,515: Notice of Publication, dated Dec. 18, 2014, 1 page.
U.S. Appl. No. 13/916,515: Requirement for Restriction/Election, dated Feb. 5, 2015, 6 pages.
U.S. Appl. No. 13/916,515: Response to Election/Restriction Filed, Mar. 19, 2015, 12 pages.
U.S. Appl. No. 13/916,515: Non-Final Rejection, dated Apr. 2, 2015, 13 pages.
U.S. Appl. No. 13/916,515: Amendment/Req. Reconsideration-After Non-Final Rejection, dated Jul. 2, 2015, 21 pages.
U.S. Appl. No. 13/916,515: Final Rejection, dated Nov. 4, 2015, 15 pages.
U.S. Appl. No. 13/916,515: Response After Final Action, dated Jan. 21, 2016, 11 pages.
U.S. Appl. No. 13/916,515: Supplemental Amendment, dated Feb. 23, 2016, 9 pages.
U.S. Appl. No. 13/916,515: Notice of Allowance and Fees, dated Apr. 4, 2016, 10 pages.
U.S. Appl. No. 13/916,515: Supplemental Amendment, dated Apr. 4, 2016, 1 page.
U.S. Appl. No. 13/916,515: Issue Fee Payment, dated Jun. 14, 2016, 4 pages.
U.S. Appl. No. 13/916,515: Issue Notification, dated Jun. 29, 2016, 1 page.

PARAMETER MEASUREMENT OF PHASE OBJECTS USING TOMOGRAPHIC IMAGING

BACKGROUND

1. Field

This disclosure relates to forming portions of one or more images to represent a corresponding portion of a three-dimensional object, such as an object, to measure properties of the object.

2. Information

Many objects, such sections of fiber-optic cables, portions of biological tissues, and/or other structures may comprise relatively transparent substances and/or materials, for example, and, therefore, may be studied using image capture devices, such as to detect features, such as phase changes in illuminating light that may impinge on a portion of the object, including phase, for example. In one example, an object comprising a combination of materials, such as an optical fiber (e.g., fiber under test (FUT)), may comprise differing indices of refraction at different places within the FUT. An optical measurement system may include an interferometric microscope, as an example, to measure features of the materials, such as to detect differences in phase of illuminating light as it travels through the object in a substantially transverse oriented direction, for example, of a FUT. In at least some instances, as a non-limiting example, interferometric measurements may be performed at various angular orientations in a manner that enables construction of several two-dimensional images to represent a portion of the object undergoing study (e.g., FUT). However, typically optical measurement systems may include optics that have a limited depth of field (DOF). In some situations, optics having a limited DOF may make obtaining meaningful measurements problematic.

BRIEF DESCRIPTION OF DRAWINGS

Claimed subject matter is particularly pointed out and/or distinctly claimed in the concluding portion of the specification. However, both as to organization and/or method of operation, together with objects, features, and/or advantages thereof, claimed subject matter may be understood by reference to the following detailed description if read with the accompanying drawings in which:

Reference is made in the following detailed description to accompanying drawings, which form a part hereof, wherein like numerals may designate like parts throughout to indicate corresponding and/or analogous components. It will be appreciated that components illustrated in the figures have not necessarily been drawn to scale, such as for simplicity and/or clarity of illustration. For example, dimensions of some components may be exaggerated relative to other components. Further, it is to be understood that other embodiments may be utilized. Furthermore, structural and/or other changes may be made without departing from claimed subject matter. It should also be noted that directions and/or references, for example, up, down, top, bottom, and so on, may be used to facilitate discussion of drawings and/or are not intended to restrict application of claimed subject matter. Therefore, the following detailed description is not to be taken to limit claimed subject matter and/or equivalents.

DETAILED DESCRIPTION

In the following detailed description, numerous specific details are set forth to provide a thorough understanding of claimed subject matter. For purposes of explanation, specific numbers, systems and/or configurations are set forth, for example. However, it should be apparent to one skilled in the relevant art having benefit of this disclosure that claimed subject matter may be practiced without specific details. In other instances, well-known features may be omitted and/or simplified so as not to obscure claimed subject matter. While certain features have been illustrated and/or described herein, many modifications, substitutions, changes and/or equivalents may occur to those skilled in the art. It is, therefore, to be understood that appended claims are intended to cover any and all modifications and/or changes as fall within claimed subject matter.

Reference throughout this specification to one implementation, an implementation, one embodiment, an embodiment and/or the like may mean that a particular feature, structure, or characteristic described in connection with a particular implementation or embodiment may be included in at least one implementation or embodiment of claimed subject matter. Thus, appearances of such phrases, for example, in various places throughout this specification are not necessarily intended to refer to the same implementation or to any one particular implementation described. Furthermore, it is to be understood that particular features, structures, or characteristics described may be combined in various ways in one or more implementations. In general, of course, these and other issues may vary with context. Therefore, particular context of description or usage may provide helpful guidance regarding inferences to be drawn.

Operations and/or processing, such as in association with networks, such as computer and/or communication networks, for example, may involve physical manipulations of physical quantities. Typically, although not necessarily, these quantities may take the form of electrical and/or magnetic signals capable of, for example, being stored, transferred, combined, processed, compared and/or otherwise manipulated. It has proven convenient, at times, principally for reasons of common usage, to refer to these signals as bits, data, values, elements, symbols, characters, terms, numbers, numerals and/or the like. It should be understood, however, that all of these or similar terms are to be associated with appropriate physical quantities and are intended to merely be convenient labels.

Likewise, in this context, the terms "coupled", "connected," and/or similar terms, may be used. It should be understood that these terms are not intended as synonyms. Rather, "connected" may be used to indicate that two or more elements or other components, for example, are in direct physical and/or electrical contact; while, "coupled" may mean that two or more components are in direct physical or electrical contact; however, "coupled" may also mean that two or more components are not in direct contact, but may nonetheless co-operate or interact. The term coupled may also be understood to mean indirectly connected, for example, in an appropriate context.

The terms, "and", "or", "and/or" and/or similar terms, as used herein, may include a variety of meanings that also are expected to depend at least in part upon the particular context in which such terms are used. Typically, "or" if used to associate a list, such as A, B or C, is intended to mean A, B, and C, here used in the inclusive sense, as well as A, B or C, here used in the exclusive sense. In addition, the term "one or more" and/or similar terms may be used to describe any feature, structure, and/or characteristic in the singular and/or may be used to describe a plurality or some other combination of features, structures and/or characteristics. Though, it should be noted that this is merely an illustrative example and claimed subject matter is not limited to this example. Again, particular context of description or usage may provide helpful guidance regarding inferences to be drawn.

It should be understood that for ease of description a computer may be embodied and/or described in terms of a computing device. However, it should further be understood that this description should in no way be construed that claimed subject matter is limited to one embodiment and, instead, may be embodied as a variety of devices or combinations thereof, including, for example, one or more illustrative examples, as described later. In this context, the term computing device refers to any device capable of performing computations; such as, a desktop computer, a laptop computer, a tablet, a set top box, etc.; however, typically, a computing device may also be capable of sending and/or receiving signals (e.g., signal packets), such as via a wired or wireless network, may be capable of performing arithmetic and/or logic operations, processing and/or storing signals, such as in memory as physical memory states, and/or may, for example, operate as a client and/or as a server.

Example embodiments may involve optical measurement systems and/or devices, such as ones capable of interferometric microscopy, for example; although claimed subject matter is not so limited, as explained below. For example, other approaches to producing interference may be employed for study. Likewise, other physical phenomena other than interference may be studied. However, continuing with this non-limiting, illustrative example, in particular implementations, for example, an interferometric microscope may involve numerically synthesizing one or more portions of one or more images of a three-dimensional object using a combination of amplitudes and/or phases of illuminating light that may impinge on an object relative to a reference beam and, therefore, may result in optical interference. If beams are combined at a planar detector array, for example, an interference pattern may result, at least in part, from superposition. Locations on a detector array may realize constructive superposition and may appear as relatively bright. Likewise, locations on a detector array may realize destructive superposition and may appear relatively dark. Of course, a range of gradations of light and dark likewise may result.

Accordingly, example embodiments may use imaging to perform measurements of an object, such as a "phase object," for example, without limit. A phase object may be characterized as an object that may not absorb a significant amount of illuminating light, for example. As explained, other objects may nonetheless be studied. In one instance, as an illustrative example, a phase object may correspond to a transparent or semi-transparent glass fiber having a uniform or non-uniform index of refraction. Thus, for example, portions of illuminating light incident on a phase object that may traverse a region of higher refractive index may appear out of phase with respect to portions of an illuminating light beam that may have traversed regions of lower refractive index. In other instances, a phase object may exhibit birefringence, in which illuminating light polarized along a first orientation may experience a different phase change from illuminating light polarized along a second orientation.

In still other instances, not necessarily corresponding to phase or angular orientation, an object under investigation (e.g., FUT) may exhibit characteristics of an object at a first range of wavelengths and may not exhibit characteristics of an object at a second range of wavelengths. For example, an erbium doped traveling-wave fiber amplifier may exhibit amplified spontaneous emission at approximately 1550.0 nanometers at least partially responsive to a pumping energy signal at approximately 980.0 nanometers. However, these are merely examples of objects, and claimed subject matter is not intended to be limited to these examples. Rather, claimed subject matter is intended to embrace all types of objects, which may include various types of materials and/or substances, such as portions of biological tissues, segments of crystalline material, relatively transparent (e.g., non-attenuating) compressible and/or incompressible fluids, and so forth.

For example, in an embodiment, an object may comprise an object capable of energy emission, such as emission of light. For example, energy may be pump through an erbium-doped fiber, such as using propagation of 980.0 nm light through the fiber and a detector may be employed to measure spontaneously emitted light at a multiplicity of angular orientations and/or focal positions. In an embodiment, a reconstruction of a relatively high-fidelity rendition of spatial distribution of emission from in the fiber may be generated even in situations in which a DOF is much smaller than a transverse dimension of the fiber, for example. In this non-limiting example, there is not necessarily a reference beam, interference fringes, or measurement of phase employed; rather, measurement of amplitude of spontaneously emitted radiation may be employed to generate a desired spatial distribution.

As another example, in another embodiment, an object may comprise an object capable of energy absorption, such as absorption of light. For example, a detector may be used to detect radiation not absorbed by a specimen or object, for example. Measurements may, for example, be acquired over a multiplicity of angles at a multiplicity of focal positions and combined in an embodiment, for example, to yield a relatively high-fidelity rendition of a cross section of the object of specimen even in situations in which a DOF is much smaller than a transverse dimension of the specimen, for example. Again, in this non-limiting illustration, there is not necessarily a reference beam or interference fringes; rather, measurement of amplitude and phase may be employed to generate a desired cross-section.

Embodiments described are non-limiting illustrative examples. As another example, an embodiment may perform one or more image capture operations at various orientations, such as differing relative angular displacements and/or differing relative positional displacements (e.g., horizontal) with respect to an object being measured, for example. In one possible example, a FUT may be observed at approximately 18.0° increments around an exterior surface of a circular or elliptical cross-section. However, in other examples, objects may be observed at smaller increments of relative angular orientation, such as approximately 1.0°, approximately 5.0°, approximately 10.0°, and so forth, or may be observed at larger increments of relative angular orientation, such as 30°, 45°, or 60°, etc. In implementations, as part of an image capture operation, an object may undergo displacement relative to an image capture device, such as a positional displacement and/or angular displacement, for example. If an object were to be rotated, for example, an image capture device may be rotated or both may be rotated to produce a relative angular displacement. Likewise, as described in more detail later, relative horizontal displacement between an image capture device and an object may take place, such as by moving an image capture device, an object, or both. In one embodiment, an object, such as an optical fiber, may be rotated about its axis by a chuck mechanically coupled to a manually controlled, or computer controlled, rotating actuator, as a non-limiting illustrative example.

An optical measurement system, such as used in imaging as previously discussed, may include optics, such as a system of lens, collimators, mirrors, beam splitters, etc., which in combination may result in an effective limited depth-of-field (DOF). In this context, the term light refers to electromagnetic radiation at any wavelength or frequency and the term optical spectrum or optical spectra refers to a range of wavelengths or range of frequencies of electromagnetic radiation. Radiation may correspond to x-rays, ultraviolet light, visible light, infra-red light. Terahertz radiation, microwaves, or radio waves. Depth-of-field in this context refers to as a maximum movement of an object plane away from an ideal object plane that is able to be made without substantial degradation in one or more optical measurements. DOF will typically be limited since infinite DOF or near infinite DOF may not be physically realizable. Beneficially high spatial resolution may be associated with an imaging system incorporating a microscope objective lens whose numerical aperture (NA) is relatively high, for example 1.0, in which case depth-of-field will typically be correspondingly relatively small. In this context, the term optical measurement system refers to a system that employs electromagnetic radiation to detect features of an object. Furthermore, an optical measurement system, as an example, here may include a device capable of capturing images, (e.g., an image capture device), which may, as examples, include silicon CCDs and/or CMOS sensors, InGaAs detectors, HgCdTe or MCT detectors, as well as components for performing processing of captured imaged.

Although not necessarily, for purposes of convenience of discussion, we assume optics are part of an image capture device in an embodiment; however, claimed subject matter is not limited in scope in this respect. Likewise, an object, such as a FUT, for example, may comprise a dimension, such as in a substantially transverse orientation, larger than a depth-of-field of optics of an image capture device included in an optical measurement system. For example, an object being observed may comprise a depth of, for example, approximately 100.0 microns, and optics of an image capture device may comprise a depth-of-field of, for example, approximately 1.0 microns. In such an instance, for example, an image capture device may perform approximately 100 measurements at increments of approximately 1.0 micron through relative horizontal displacement to produce a plurality of substantially parallel focal planes, beginning with focusing on a region farthest from the optics, as an example. Accordingly, if an image capture device having optics with a depth-of-field of approximately 1.0 micron performs a measurement, for example, at a focal length of 50.0 microns, for example, portions of an object at a range of approximately 0.0 to approximately 49.5 microns and at a range larger than approximately 50.5 micron may appear to be out-of-focus. A portion of an object between approximately 49.5 microns and 50.5 micron may appear to be in-focus. It should be noted, however, that claimed subject matter is not limited to specific depths of objects being observed, image capture devices having specific ranges of depth-of-field, specific measurement increments, specific orders in which measurement operations may be conducted (e.g., furthest to nearest, nearest to furthest, etc.), and so forth. In an implementation, to reduce size of a sample of measurements and/or reduce acquisition (e.g., computation) time, it may be convenient to sample a 100.0 micron wide object at intervals. such as 5.0 microns or 10.0 microns, for example, thereby using an increment that is larger than a nominal depth-of-field.

For example, in an instance, light captured by an image capture device to obtain measurements may include in-focus and out-of-focus components combined, as described in more detail later. A two-dimensional image (e.g., image frame, matrix of measurements, or one or more portions thereof) may comprise a plurality of combined measurements. In this case, a pixel of a two-dimensional image (or portion thereof) may comprise a distinct measurement, for example, corresponding to a distinct three dimensional spatial location of an object (e.g., in an embodiment corresponding to a relative angular orientation and/or relative depth with respect to system optics). A distinct measurement may, therefore, in an embodiment be generated responsive to detecting changes in measurements at a plurality of focal lengths corresponding to a plurality of substantially parallel focal planes comprising near and far boundaries of an object and between the boundaries, for example.

In one embodiment, a focal plane corresponding to a mid-section, or "zero" position, of an optical fiber may be used to characterized a depth of a focal plane at which outer edges of a fiber's cladding surface may exhibit a phase gradient larger than at alternative depths, as a non-limiting example. Thus, for example, in an embodiment, depth may refer to a substantially horizontal position relative to a zero position, such as in this non-limiting illustrative example. At other focal planes, an edge of a fiber may be out-of-focus and may therefore exhibit a lesser phase gradient. Alternatively, as another non-limiting illustrative example, a focal plane may be identified as the mid-section, or "zero" position, where a phase gradient at an edge of a fiber's core is larger than at alternative depths. Of course, claimed subject matter is not limited to a phase gradient or even any gradient to select a "zero position." Any one of a host of approaches are possible and claimed subject matter is not limited to a particular approach.

In an embodiment, a zero position may be employed to characterize a unified coordinate system relative to a particular three dimensional spatial location, such as at a particular angular orientation and particular depth, for example, relative to system optics, for example, as also described in more detail later.

Embodiments may utilize one or more signal processing-type transforms. For example, for improved computational efficiency, processing may be performed in the transform domain, such as using a Fourier transform or other approach. For example, as discussed in more detail below, two-dimensional image frames (or portions thereof) from an image capture device may be processed. Other embodiments may make use of Radon transforms, and/or other continuous or discrete transforms to convert complex-valued functions of amplitude and/or phase. Of course, claimed subject matter is not limited to a particular transform.

Figure 1:
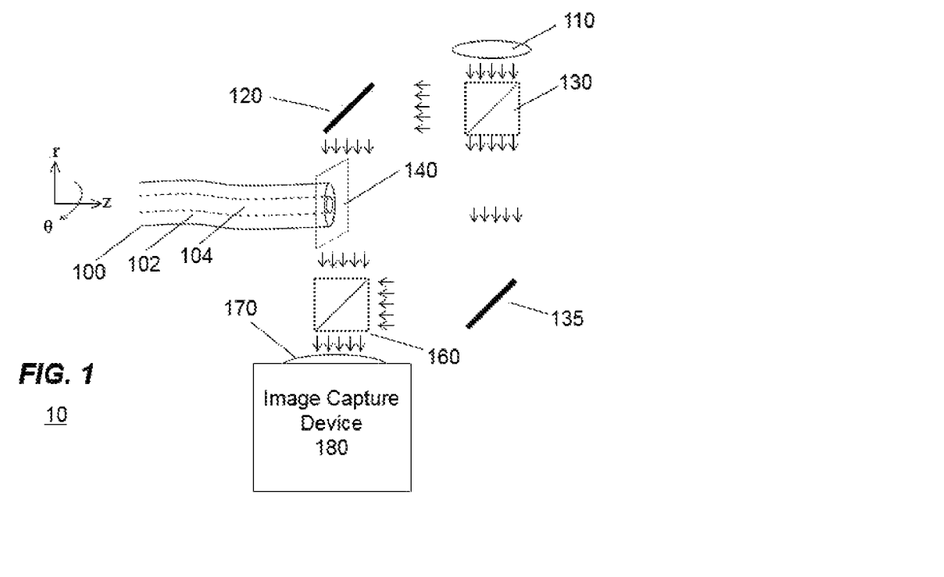
FIG. 1 is a schematic diagram illustrating a system for tomographic imaging according to an embodiment.

If measurements are not transformed into an alternative domain, they may, for example, be algebraically convolved with a filter, such as a Ram-Lak filter Shepp-Logan filter, a Hamming filter, a cosine filter, or other filtering scheme. If, however, measurements are transformed to an alternate domain, such as to a frequency domain, for example, the transformed measurements may be multiplied by a filter, such a ramp filter, a Ram-Lak filter, a Shepp-Logan filter, a Hamming filter, a cosine filter, or other filtering scheme, or combinations thereof. Likewise, an inverse transform may be used after multiplication by a filter. Furthermore, as described in more detail below, filtered two-dimensional image frames (or portions thereof) of measurements may be combined in a unified coordinate system, such as, for example, via linear operations, such as to rotate and/or translate, and to at least partially superposition processed measurements to form an image (or portion thereof) of a corresponding portion of an object, such as a FUT, for example FIG. 1 is a schematic diagram of a system for tomographic imaging of a three-dimensional object, such as an object, according to an embodiment 10, for example. In FIG. 1, object 100 represents an object being observed by way of image capture device 180, such as a FUT. FUT 100, which may represent a portion of a single-core optical fiber, for example, may extend axially in a +z direction and may comprise features, such as cladding 102, for example, located at various positions along radius r and with respect to angle θ, as shown in FIG. 1. Of course, claimed subject matter is not limited to illustrative examples, such as shown in the figures. At least in some embodiments, manufacturing processes used in constructing FUT 100 may be intended to produce a fiber, for example, having predictable and/or reasonably consistent features that may, for example, vary as a function of position, such as radius r, e.g., for regions comprising specific ranges of index of refraction, for example; nonetheless, verification of features and/or quality control processes may be desirable. Further, although manufacturing processes may be, for example, intended to produce fiber, for example, having desired features, such as rotationally symmetric features, for example, again, verification and/or quality control of features and/or fabrication processes may be desirable. It should be noted, that although FUT 100 may correspond to an optical fiber, as previously indicated, a variety of other objects may be observed, such as crystalline structures, biological samples, plastic films, capillary tubes, and many other objects. Again, claimed subject matter is not limited to illustrative examples.

System embodiment 10 of FIG. 1 may correspond, for example, to an interferometric microscope, such as a Mach-Zehnder interferometer, for example, although embodiments may also correspond to other systems and/or arrangements of equipment in which interferometric phenomenon may be used and/or in which other types of physical phenomena other than or in addition to interferometric phenomenon may be used to study and/or observe objects, such as, for example, refractive index, spontaneous emission, optical absorption, and/or other properties, for example.

In the embodiment of FIG. 1, illumination source 110 may represent, for example, a source of electromagnetic radiation to impinge on mirror 130. Mirror 130 may comprise, at least in some embodiments, a beam splitter in which approximately 50.0% of incident light may be transmitted toward object 100 and approximately 50.0% of incident light may be transmitted toward mirror 135. Mirror 135, for example, may reflect approximately 100.0% of incident light toward mirror 160, which may direct approximately 50.0% of incident light toward lens 170 of image capture device 180. Mirror 120, for example, may direct 100.0% of incident light towards mirror 160, which may direct approximately 50.0% of incident light towards lens 170 of image capture device 180. Again, this is intended as a non-limiting illustrative example. Other embodiments of image capture devices may be more complex or less complex, for example.

Light from mirror 120 may pass through a plane 140 intersecting an object, for example, oriented in a substantially transverse direction relative to an object, such as FUT 100, for example. In this context, a substantially transverse direction refers to a direction in a plane, such as 140, the plane being oriented substantially perpendicular to propagation of light through the object during expected use, such as for FUT 100. In embodiments, light transmitted to take measurements may be oriented in a substantially transverse direction, such as 140, relative to FUT 100, so as to exhibit changes in an index of refraction substantially as a function of a position, such as radially from a center axis of an object, as an example. For example, core 104, which may be surrounded by cladding 102, may comprise a higher index of refraction than material outside of cladding 102. Accordingly, incident light traversing core 104, for example, may travel at a different speed than light traversing across cladding 102, for example. Using an interferometric microscope, such as an interferometric microscope in accordance with that of FIG. 1, for example, as a non-limiting example, changes in phase may be observed at a substantially planar detector array of image capture device 180. As indicated, likewise, in other embodiments, other measurements other than phase are likewise capable of being made. However, in the embodiment of FIG. 1, for example, variations in phase, if combined with a reference illumination from beam splitting mirror 130 and 160, and mirrors 135 and 120, may be stored by image capture device 180, for example. Again, it should be noted, however, that the particular arrangement of components in FIG. 1 represents one of many possible arrangements, and claimed subject matter is not intended to be limited in this respect.

Figure 2:
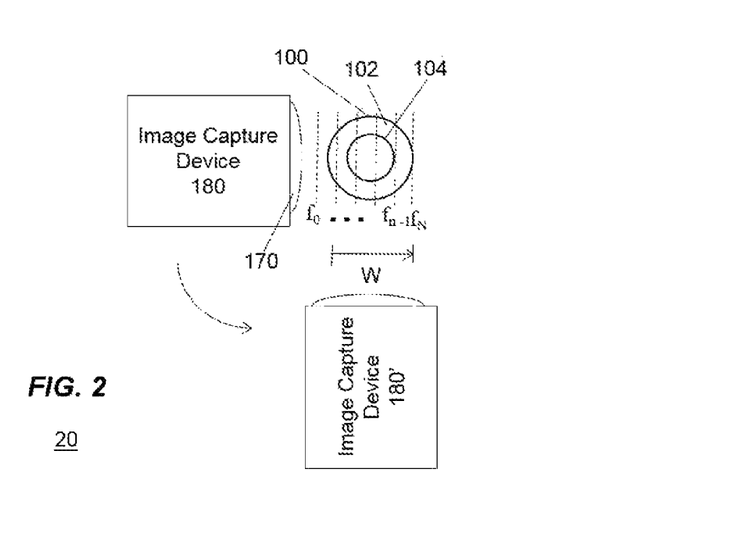
FIGS. 2, 3, 4, 5, and 6 are schematic diagrams of additional illustrations of the system of FIG. 1.

FIG. 2 is a schematic diagram of a system for tomographic imaging using an image capture device positioned at various orientations, such as for example, positional and/or angular, relative to an object according to an embodiment. FIG. 2 may correspond, for example, to a portion of a system 10 of FIG. 1, in which plane 140 may be oriented substantially in the plane of the page. Accordingly, image capture device 180' may represent image capture device 180 of FIG. 1 at a different angular orientation relative to FUT 100. As previously mentioned, image capture device 180 may represent a component of an optical measurement system. A feature may, for example, include a depth-of-field that may, at least in some embodiments, comprise a distance that is less than an overall object width, given by W in FIG. 2 (e.g., depth-of-field<<W), relative to image capture device 180, also referred to here as depth. Thus, as shown, a width W may be oriented substantially parallel to a direction of light propagation in this example. It is noted that here, since the object has a circular shape oriented along plane 140, the width does not change regardless of relative angular orientation from 180 to 180', for example. For objects of another shape, the greatest width through the object lying in plane 140 taking into consideration any relative angular orientation may be an appropriate comparison with DOF. In general, object cross section need not be circular and may, for example, be polygonal, elliptical or otherwise comprise a non-circular closed geometric shape.

If a depth-of-field of image capture device 180 comprises a significantly smaller distance than object width W, image capture device 180 may be focused through relative movement in a substantially horizontal direction between object and image capture device, beginning with, for example, a focal length $f_n$, which may correspond to a boundary of FUT 100. An image frame, comprising changes in measured signal parameters with respect to a reference beam, such as, for example, amplitude, frequency, and/or phase, for example, may be captured by way of device 180. Device 180 may be refocused, for example, to a location nearer to objective lens 170, such as $f_{n-1}$, again, via relative movement. For example, in an embodiment, a stepper motor may be employed to move the device and/or the object. A second image frame may be captured by device 180 focused at $f_{n-1}$, and the device may be refocused to a third location such as $f_{n-2}$. In general, a focal plane may be moved by moving an object, such as 100, by moving an imaging lens, such as 170, and/or by moving an image capture device including optics, such as 180. In embodiments, a process of image frame capture, refocus, and image frame capture, may be repeated until an image frame is captured at a distance $f_0$, which, for example, may correspond to a distance immediately adjacent lens 170, in this example. In a further embodiment, a focal position may be scanned continually while distinct images (or portions thereof) corresponding to different focal positions may also be acquired from an image capture device. It should be noted, that although in this illustrative example imaging is described as being performed beginning with a distance at a near point from objective lens 170 and continuing in decrements, embodiments may begin with, for example, focusing one or more lenses to a distance closest to an objective lens and continuing in increments until reaching, for example, a far point, or even yet another approach to adjusting relative position via relative motion, so as to provide a plurality of substantially parallel focal planes. Likewise, it is not required that increments or decrements, for example, be consistently sized, although they may be consistently sized out of convenience as well.

In an embodiment, image capture device 180 may include a planar detector array having a number of picture elements or "pixels" that may number from perhaps as few as 10 or 20, or may number into the thousands, hundreds of thousands, millions, and so forth arranged in a rectangular array, for example. Of course, claimed subject matter is not limited to a rectangular detector array. An array may comprise a 1-dimensional linear array of pixels. Alternatively, a linear array of pixels may be approximated by a single pixel detector combined with an optical scanning device that may relatively rapidly map different transverse object positions to a single-pixel detector. Alternatively, a two-dimensional array may be approximated by a linear array detector combined with an optical scanning device or a single-pixel detector combined with a raster scanning device.

Nonetheless, in one embodiment, continuing with a non-limiting illustrative example, a detector array may comprise approximately 1000 to 1500 optical light sensors, such as charge-coupled devices and/or CMOS sensors, for example, oriented to be in a plane substantially parallel to the plurality of focal planes. Accordingly, for a given image capture operation, such as at a particular focal length $f_n$, charge-coupled devices of a detector array oriented substantially parallel to the focal plane formed may be aggregated and/or averaged, as described in more detail later, for example. It should be noted; however, that image capture devices, such as device 180 of FIGS. 1 and 2, may include any number of devices in a planar or non-planar detector array. Likewise, the sensors may be arranged in any shape. Further, image capture devices may employ a range of detector technologies, including those now known, such as charge-coupled devices and/or complementary metal oxide semiconductor (CMOS) sensors, InGaAs arrays, and/or HgCdTe detectors, as previously suggested, or later developed, etc.

Although not shown in FIGS. 1 and 2, core 104 of object 100 may comprise a region doped with a rare earth element, such as erbium, neodymium, ytterbium, thulium, praseodymium, holmium, and/or silicates, phosphates, fluorides, fluorozirconates, or other admixtures and compounds. In one embodiment, object 100 may represent an erbium-doped traveling-wave fiber amplifier exhibiting amplified spontaneous emission at approximately 1550.0 nanometers responsive to a pumping energy signal at approximately 980.0 nanometers, for example. In an embodiment, image capture device 180 may measure amplitude and/or other signal parameters of spontaneous emissions in a manner that may enable verification, for example, of amplifier parameters, such as emission wavelength, optical gain efficiency, spatial distribution of optical gain, spectral purity, power density, and so forth, of an optical fiber intended to exhibit amplified spontaneous emission. Again, however, claimed subject matter is not limited to an illustrative example, such as this.

In an embodiment, core 104 of object 100 may comprise a region at which wavelength-selective attenuation may occur. For example, an optical fiber may attenuate electromagnetic energy at, for example, wavelengths near an absorption peak such as 976.0 nanometers, for example. In an embodiment, image capture device 180 may measure signal amplitude and/or other signal parameters (e.g., phase and/or frequency) and/or changes thereof for an illuminating beam comprising energy at wavelengths of approximately 976.0 nanometers. Again, claimed subject matter is not limited to an illustrative example.

Figure 3:
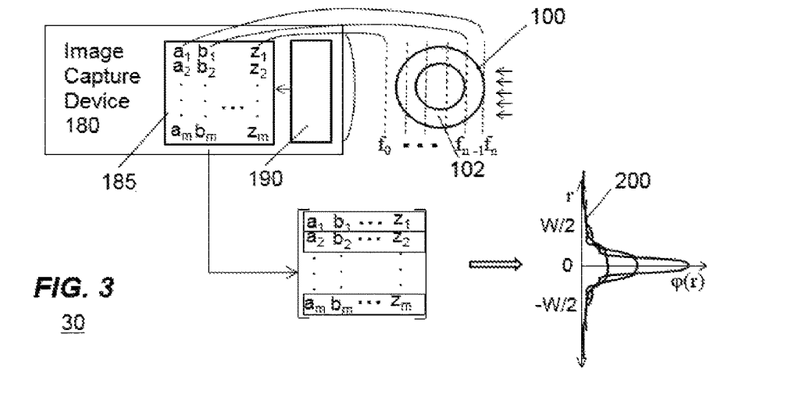

FIG. 3 is a schematic diagram of a tomographic imaging device that may be used to measure characteristics of an object according to an embodiment 30. In FIG. 3, memory array 185 is coupled to planar detector array 190, which may detect electromagnetic radiation corresponding to pixel locations in a manner to measure signal parameter changes of an illuminating beam that may impinge on FUT 100. Thus, a first column of values, such as $a_1, a_2, \ldots, a_M$ may represent, for example, a one-dimensional vector comprising measurements of an average value of signal parameter deviations from an illuminating beam at a focal length corresponding to $f_n$. Likewise, a second column of values, such as $b_1, b_2, \ldots, b_M$ may represent, for example, a one-dimensional vector comprising measurements of average value of signal parameter deviations from an illuminating beam at a focal length corresponding to $f_{n-1}$. Likewise, an additional column of values, such as $z_1, z_2, \ldots, z_M$ may represent, for example, a one-dimensional vector comprising measurements of average value of signal parameter deviations from an illuminating beam at a focal length corresponding to $f_0$. In an aforementioned example, a subscript "M" may refer to a number of pixels in a vertical direction such as, for example, approximately 1000 pixels as described with reference to FIG. 2.

As shown in FIG. 3, measurements from image capture device 180 may be used to generate a set of distinct 1-dimensional signal parameter profiles, respectively acquired at different focal positions. A 1-dimensional signal parameter measurement profile may result from a single row of image capture device 180, alternatively, may be formed by an averaging of one or more rows of image capture device 180, or may be formed using a single pixel detector, such as previously described, for example. Three 1-dimensional signal parameter profiles acquired at different focal positions are shown in chart 200. To illustrate, if image capture device 180 is focused at a focal length of $f_n$, for example, features present at, for example, a focal length $f_{n-1} \ldots, f_0$ may be observed by planar detector array 190 as out-of-focus. Likewise, if image capture device 180 is focused to a focal length of $f_{n-1}$, for example, features present at focal length $f_n$ as well as $f_{n-2}$ through $f_0$ may be observed by planar detector array 190 as out-of-focus. Accordingly, measurements performed by image capture device 180, by way of planar detector array 190 and stored in memory array 185 as, a one-dimensional vector $a_1$, $a_2, \ldots, a_M$ may include contributions from in-focus components of FUT 100 as well as contributions from out-of-focus components of FUT 100. Likewise, measurements performed by way of planar detector array 190 and stored in memory array 185 as a one-dimensional vector $b_1$, $b_2, \ldots, b_M$ may include contributions from in-focus and out-of-focus components of FUT 100. In an embodiment, a plurality of signal parameter profiles, such as those described may be combined, such as by being at least partially overlaid via superposition, for example, as described below.

In an embodiment, 1-dimensional profiles depicted in chart 200 of FIG. 3 may comprise signal parameter deviations of an illuminating beam that may impinge on FUT 100 relative to a reference beam, such as for a particular relative angular orientation, for example. Near a center portion of chart 200, a relatively large phase deviation may, for example, be seen. In embodiments, a relatively large phase deviation may be at least partially in response to optical delay of an illuminating beam impinging on FUT 100 at an approximate right angle to a boundary of cladding 102. Here, for example, three different profiles shown in chart 200 may correspond to an optical phase delay measured across core 102 at three different focal positions for a particular relative angular orientation. Of course, claimed subject matter is not limited in scope to this illustrative example.

Figure 4:
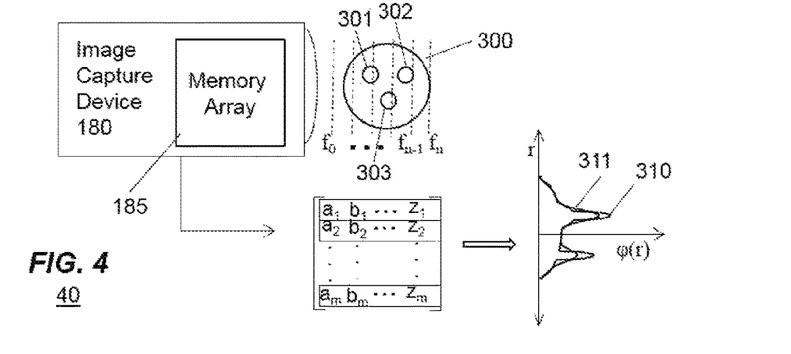

FIG. 4 is a schematic diagram of the tomographic imaging device embodiment of FIG. 3 according to an embodiment. In FIG. 4, FUT 300 may represent, for example, an optical fiber having a more complex construction than 100, for example. FUT 300 may be seen as comprising three cladded regions, such as features 301, 302, and 303, as opposed to a single cladded region, such as region 102 of FIG. 1. In accordance with one or more previously described embodiments, memory array 185 of image capture device 180 may store signal measurements corresponding to portions of object 300 at focal lengths of $f_n, f_{n-1}, \ldots, f_0$. Individual measurements stored within memory array 185 may comprise in-focus and out-of-focus contributions. For example, signal parameter profile 310 may correspond to measurements acquired for a focal plane intersecting feature 302. Signal parameter profile 311 may corresponds to measurements acquired for a focal plane intersecting feature 303. It is seen that phase fluctuations corresponding to regions 301, 302, and 303 may be smeared by an amount that at least approximately scales with a substantially horizontal distance between a feature and a location of a focal plane. For a focal plane coinciding with a feature, however, it appears in reasonably sharp focus. By contrast, for a focal plane far away from a feature, a portion of a profile corresponding to that feature may be blurred.

Figure 5:
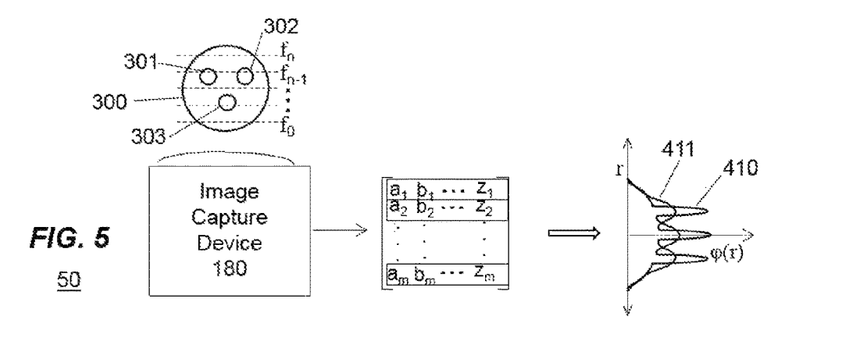

FIG. 5 is a schematic diagram of the tomographic imaging device embodiment of FIG. 4 at a different relative angular orientation according to an embodiment. In FIG. 5, image capture device 180 is shown as being rotated counterclockwise 90° relative to its position in FIG. 4. Accordingly, measurements of signal parameter deviations brought about by features 301, 302, 303, may be indicated by phase delays 410 and 411, depending at least in part on focal position. In profile 410, features 301 and 302 in this example are intersected by a focal plane whereas feature 303 is relatively far from a focal plane. By contrast, in profile 411, features 301 and 302 are relatively far from a focal plane whereas feature 303 is intersected by a focal plane in this example.

Figure 6:
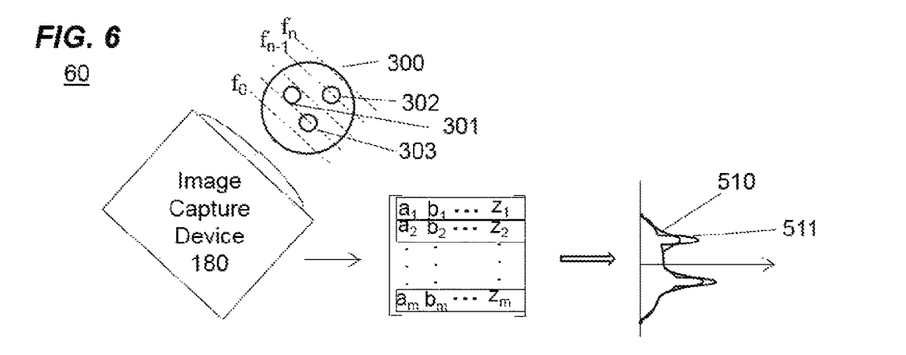

FIG. 6 is a schematic diagram of the tomographic imaging device embodiment of FIG. 4 at another different relative angular orientation according to an embodiment. In accordance with previously described embodiments, a detector array of image capture device 180 may be seen as giving rise to signal delays 510 and 511, for example. In a manner similar to that of FIG. 4, delays 510 may correspond to a focal plane intersecting feature 302 while not intersecting features 301 and 303. Delays 511 may correspond to a focal plane intersecting features 301 and 303, but not intersecting feature 302, for example.

As can be seen from FIGS. 4, 5, and 6, measuring signal parameter changes of a illuminating beam that impinges on an object, such as FUTs 100 and 300, for example, may result, at least in part, in image frames (or portions thereof) of measurements that indicate signal changes with respect to a width of an object (also referred to as depth in this context). Further, although an object may be observed using a focal length suitable for observing a portion of an object, out-of-focus contributions appear not to significantly distort resulting measurements with appropriate processing.

Figure 7A:
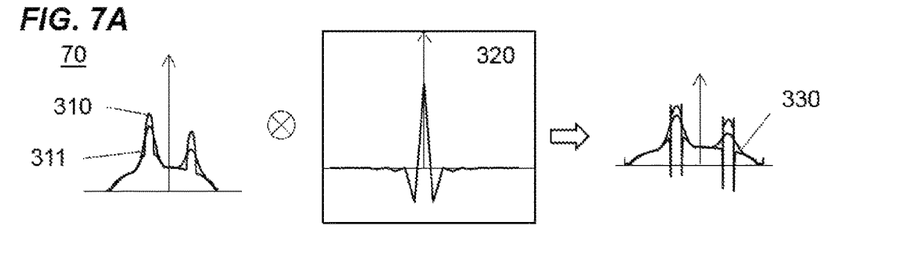
FIGS. 7A, 7B, 7C, 8, and 9 are plots to illustrate processing of optical measurements according to an embodiment.
Figure 7B:
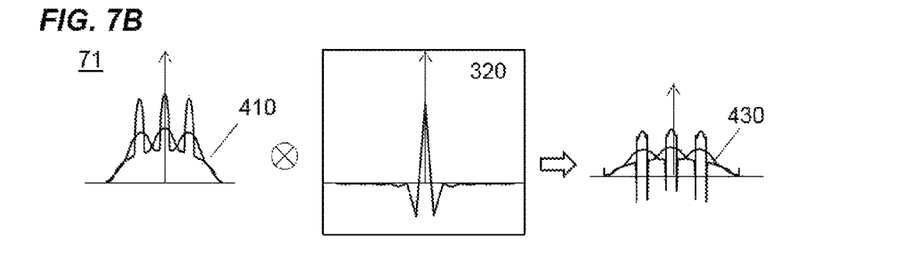
Figure 7C:
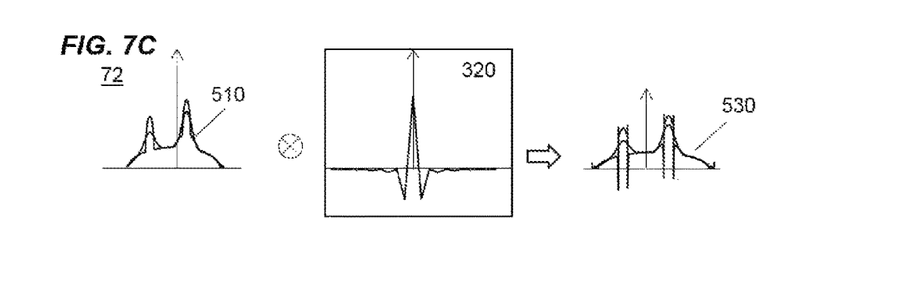

FIGS. 7A-C show representations 70, 71, and 72, which illustrate processing of output signals from an image capture device according to an embodiment. Beginning with FIG. 7A, image frame 310, from FIG. 4, for example, may be convolved, as indicated by the "⊗" in FIGS. 7A, 7B, 7C, with a filter 320, which may result in filtered image frame 330 (or a portion thereof). In embodiments, filter 320 may comprise a "Ram-Lak" (Ramachandran-Lakshminarayan) filter, for example. However, claimed subject matter is not limited in this respect. For example, in other embodiments, filter 320 may comprise a Shepp-Logan filter, a Hamming filter, a cosine filter, or any other suitable filter. However, in at least some embodiments, a selected filter should appropriately condition a signal parameter profile, such as 310, to attenuate relatively low-frequency noise that may be present, for example. Again, claimed subject matter is not limited to particular selections of frequency filtering, rolloff rates, cutoff frequencies, or other filter parameters. Filter 320 may likewise be employed to perform filtering involving convolution of 410, which may result in filtered image frame 430 (or portion thereof). Filter 320 may also be convolved with 510, which may result in filtered image frame 530 (or portion thereof).

Figure 8:
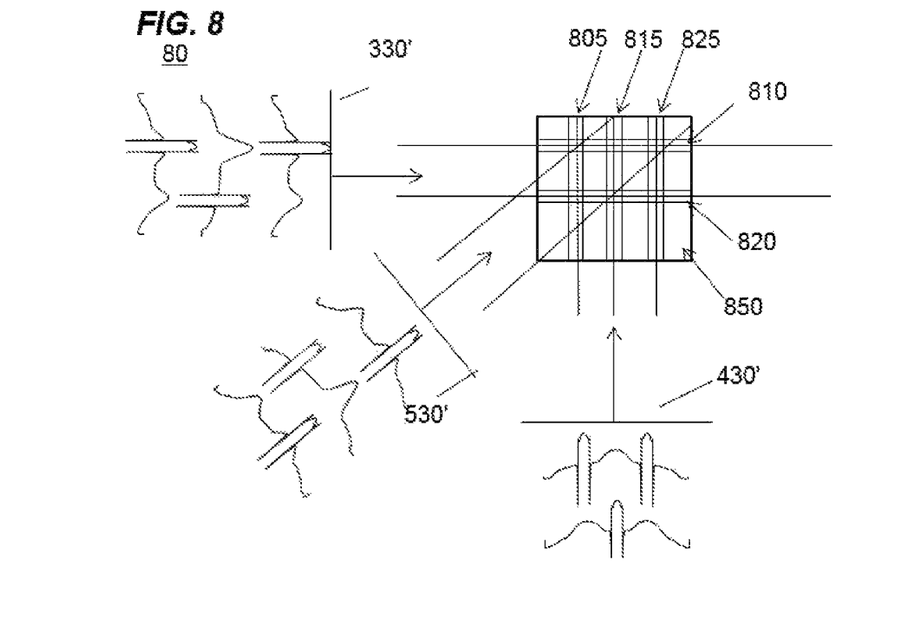

FIG. 8 is a representation of projection of filtered image frames (or portions thereof) according to an embodiment. In FIG. 8, filtered frames (or portions of frames) that may result from image capture and filtering operations previously described herein may be projected onto a unified coordinate plane through appropriate signal processing. In embodiments, an ordered set of filtered profiles, such as 330, 430, and 530, may undergo a rotation operation, such as a matrix rotation, to enable an ordered set of filtered profiles to be reoriented in a manner that permits projection onto a unified coordinate plane for at least partial superposition. For example, two-dimensional points, such as points in a Cartesian X-Y coordinate system, may be rotated by a matrix manipulation computer program, such as Matlab developed by the MathWorks Company and located at 3 Apple Hill Drive, Natick, Mass. 01760-2098 (www.mathworks.com), although, of course, this is merely a non-limiting example.

As previously described, in one embodiment, a focal plane corresponding to a mid-section, or "zero" position, of an optical fiber may be used to characterized a depth of a focal plane at which outer edges of a fiber's cladding surface may exhibit a signal parameter gradient larger than at alternative depths, as a non-limiting example. Thus, for example, in an embodiment, depth may refer to a substantially horizontal position relative to a zero position, such as in this non-limiting illustrative example. At other focal planes, an edge of a fiber may be out-of-focus and may therefore exhibit a lesser gradient. Alternatively, as another non-limiting illustrative example, a focal plane may be identified as the mid-section, or "zero" position, where a gradient at an edge of a fiber's core may be larger than at alternative depths. In an embodiment, a zero position may be employed to characterize a unified coordinate system relative to a particular three dimensional spatial location, such as at a particular angular orientation and particular depth, for example, relative to system optics, for example. Thus, a zero position, or other position if more convenient in an alternative embodiment, may, for example, represent a geometric reference point for a unified coordinate system so that signal parameter measurements profiles (e.g., signal profiles or signal parameter profiles) acquired using different focal planes, for example, are capable of being at least partially overlaid, as described in more detail below.

In FIG. 8, a two-dimensional matrix (or portion thereof) representing filtered profiles 330 (of FIG. 7) may be shown as undergoing 180° rotation to form filtered phase profiles 330'. Filtered profiles 330' may project two local maxima, which may form horizontal band 810 and 820 of coordinate plane 850, as an example. Likewise, an ordered set of filtered phase profiles 430 (FIG. 7) may be shown as undergoing a small or perhaps no rotation to form 430'. 430' may project three local maxima, which may form vertical bands 805, 815, and 825 may intersect horizontal band 820 and horizontal band 810. An ordered set of filtered profiles representing 530 (FIG. 7) may be shown as undergoing a counterclockwise rotation of 45° to form 530'. 530' may project two local maxima, which may intersect horizontal band 820 and horizontal band 810, again, as an example. Additionally, local maxima of 530' may additionally intersect vertical bands 805 and 825, for example. In FIG. 8, areas of coordinate plane 850 that are intersected by local maxima of filtered frames (or portions thereof), such as 330', 430', and 530', may correspond to features 301, 302, and 303 of FUT 300, for example. Thus, a plurality of profiles may in an embodiment, for example, be overlaid via superposition on a unified coordinate plane, such as previously mentioned.

From FIG. 8, one may appreciate that any number of two-dimensional matrices (or portions thereof) representing ordered sets of filtered profiles may be projected in an appropriate fashion onto a unified coordinate plane, such as coordinate plane 850. Likewise, as previously described, a single point of geometric reference, such as for example, a center of cladding of a fiber, may be employed to accurately and at least partially superposition a set of filtered profiles for a consistent geometric location of features. In some embodiments without limitation, filtered profiles oriented at certain relative angular orientations, such as 330', 430', and 530', for example, may correspond to relative angular orientations of image capture device 180 with respect to object 300, as described with reference to FIGS. 4, 5, and 6. In particular embodiments, an image capture device may be sequentially, for example, oriented at small relative angular increments around FUT 300, for example. Thus, in at least one embodiment, an image capture device may be oriented at, for example, approximately 5.0° relative increments with respect to FUT 300. At various relative angular orientations, an image capture device may measure characteristics of FUT 300 at varying focal lengths, such as, $f_{n-1}, \ldots, f_0$, as previously described. Captured image frames (or portions thereof) may be combined, which may be filtered, such as a Ram-Lak filter, a Shepp-Logan filter, a Hamming filter, a cosine filter, or any combination thereof, just to name a few example filter types, so as to superposition a plurality of phase profiles in an embodiment. Of course, claimed subject matter is not limited to embodiments employing a particular relative angular orientation.

Two-dimensional matrices (or portions thereof) representing ordered filtered profiles may be rotated to correspond with, for example, approximately 0.0° of relative image rotation, approximately 5.0° of relative image rotation, approximately 10.0° of relative image rotation, and so forth. Thus, to measure an object at approximately 5.0° increments of relative angular rotation, approximately 72 projections (360°/72=5.0°) onto a unified coordinate system may be performed. Symmetry may permit measurement of an arbitrary object over a measurement range of merely 180° with 36 projections (180°/72=5.0°). Furthermore, an object may have intrinsic symmetry that permits measurement over a more limited subset of relative rotations. In embodiments, if locations on a coordinate plane do not coincide with grid spacing of a two-dimensional matrix, interstitial values may be interpolated using two-dimensional interpolation routines, for example. It should be noted, however, that an above-described example is not intended to limit claimed subject matter. Thus, it is contemplated that claimed subject matter may include any increments of relative angular rotation, filtering, focal lengths, and so forth.

In embodiments, prior to projecting a plurality of two-dimensional matrices (or portions thereof) onto a unified coordinate plane, such as coordinate plane 850, for example, individual matrices (or portions thereof) may be normalized. For example, if 72 two-dimensional matrices (or portions thereof) are to be projected onto a unified coordinate plane, for example, matrix components, such as signal parameter measurements, may be divided by 72, for example, so as to provide an approximately normalized contribution. Normalization may additionally result, at least in part, in reducing likelihood of saturation in a displayed image.

Figure 9:
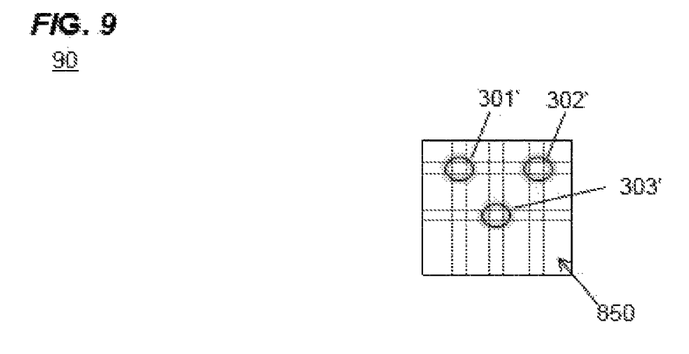

FIG. 9 is a representation of an image portion resulting from tomographic imaging according to an embodiment. As previously mentioned, areas of coordinate plane 850 that may be intersected by local maxima of filtered image frames (or portions thereof) may correspond to features of an object being observed by an image capture device. Accordingly, an object may be observed at small relative angular increments, such as approximately 5.0°, for example, in this non-limiting example, producing approximately 72 projections around a circumference of an object layered onto coordinate plane 850 in appropriate locations as superposition of a plurality of phase profiles. In FIG. 9, 301', 302', and 303', may correspond, at least in one embodiment, to features 301, 302, and 303 of FIGS. 4, 5, and 6.

Figure 10:
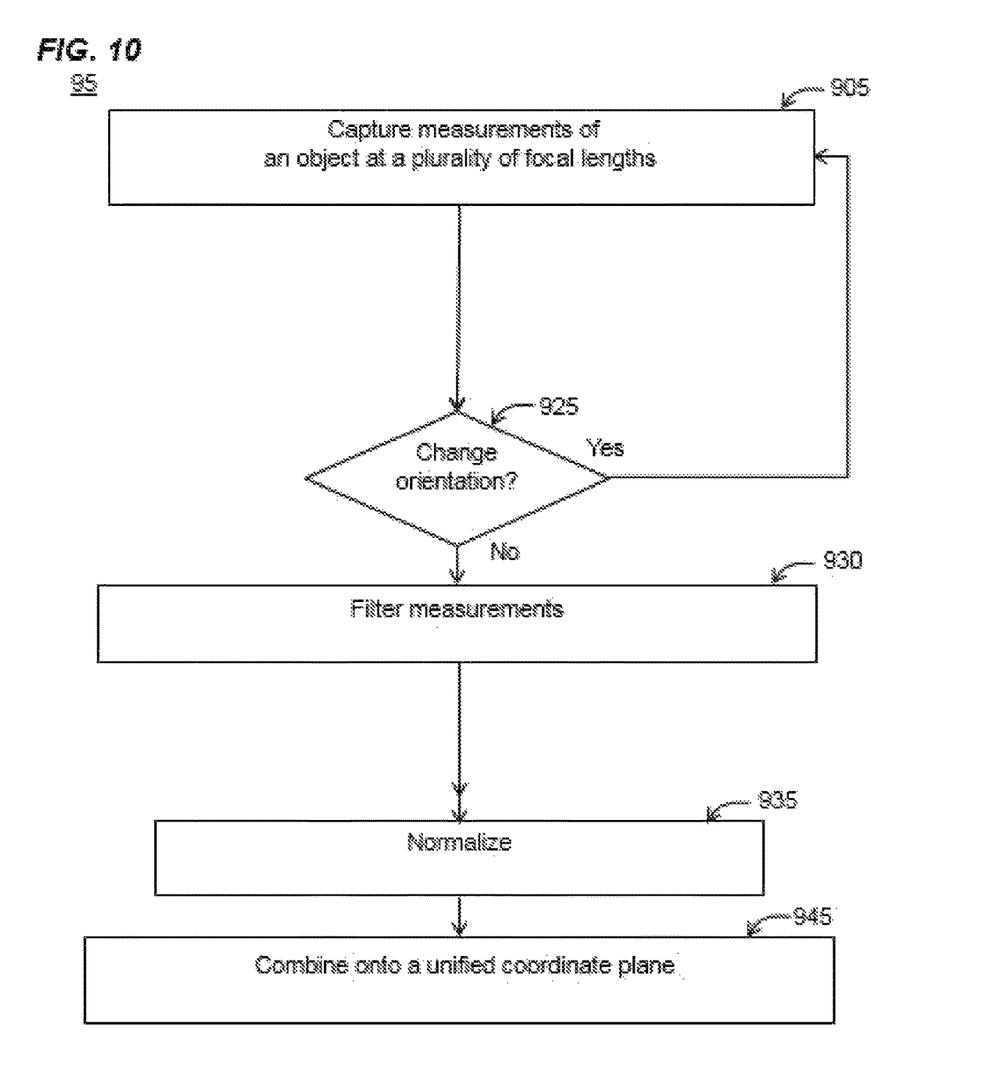
FIG. 10 is a flow chart for a method of tomographic imaging according to an embodiment.

FIG. 10 is a flowchart 95 for a method of tomographic imaging according to an embodiment. It should be understood that embodiments may include actions and/or operations in addition to those shown in FIG. 10, actions/operations occurring in a different order than shown, or may include fewer actions and/or operations as shown. Further, although FIG. 1 may be employed to perform at least portions of the method embodiment of flowchart 95, the method embodiment of flowchart 95 may be performed by alternative structures and/or components.

FIG. 10 begins at 905, in which measurements of an object may be acquired at a plurality of focal lengths from an image capture device, corresponding to a plurality of focal planes. A processor, for example, may determine a frame (or portion thereof) at which an object boundary begins. For example, an object boundary may be detected by examining a change in a measurable signal parameter of a portion of illuminating beam in relation to a reference beam. Thus, for example, a derivative of a signal parameter may be employed. In an embodiment, a center of an object may be inferred from a point located midway between object edges, for example. Alternatively, another particular feature in an image (or portion thereof) may serve as a geometric reference point for super-positioning of multiple filtered frames (or portions thereof). A two-dimensional image frame (or portion thereof) from one-dimensional projections of acquired measurements may be formed. At 925 an image capture device may be reoriented in relation to an object being observed, such as by returning to 905 and acquiring measurements of an object at various focal lengths.

At 925, a decision may be made as to whether a sufficient number of measurements of an object with an image capture device have been performed. If additional measurements are to be performed, the method embodiment may return to 905. If measurements of a sufficient number have been performed, the method embodiment may advance to 930. At 930, filtering, such as Ram-Lak filtering, Shepp-Logan filtering, Hamming filtering, and/or cosine filtering may be performed. One or more filtered image frames (or portions thereof) may be rotated in a manner that permits projection on to a unified coordinate plane. At 935, a combined matrix (or portion thereof) may be normalized in a manner that considers a number of projections of profiles at least partially overlaid onto a unified coordinate plane. At 945, rotated filtered image frames (or portions thereof) may be projected onto a unified coordinate plane.

As an alternative to the flowchart in FIG. 10, as previously alluded to, measurements at multiple relative rotations may be acquired at a single focal position. After completion of the measurements at multiple relative rotations, the focal position may be adjusted and more measurements may be acquired at multiple relative rotations. In this alternative way, as an illustrative example, measurements may be acquired at a multiplicity of relative rotations and a multiplicity of focal positions.

Figure 11:
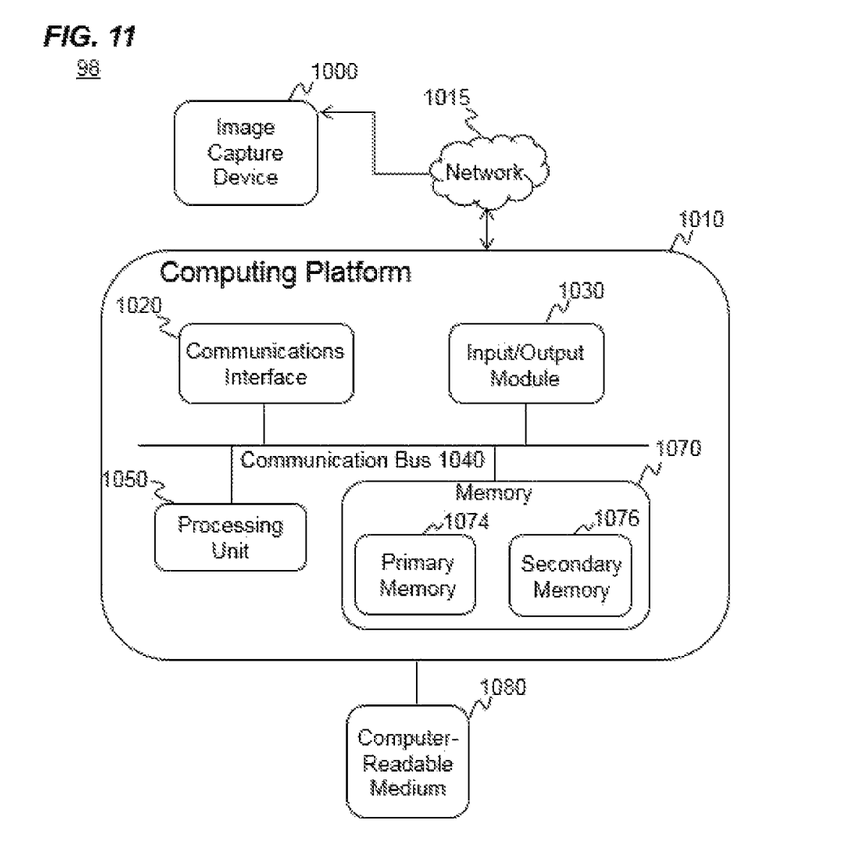
FIG. 11 is a schematic of a computing platform that may be employed to implement tomographic imaging according to an embodiment.

FIG. 11 is a schematic 98 of a computing platform that may be employed to implement multi-focus tomographic imaging according to an embodiment. For purposes of illustration, FIG. 11 is an illustration of an embodiment of a computing platform or computing device 1010 that may be employed multi-focus tomographic imaging of various types of objects, such as described infra. In FIG. 11, computing platform 1010 may interface with image capture device 1000, which may comprise features, such as of an interferometric microscope, for example. Communications interface 1020, processor (e.g., processing unit) 1050, and memory 1070, which may comprise primary memory 1074 and secondary memory 1076, may communicate by way of communication bus 1040, for example. In FIG. 11, image capture device may measure aspects of an illuminating beam that impinges on an object with respect to a reference illuminating beam at various focal lengths and/or angular orientations in a non-limiting example. Image capture device may communicate one or more of analog signal and outputs, uncompressed digital signal outputs, lossless compressed digital signal outputs, or lossy compressed digital signal outputs in the form of physical states or signals, for example. Image capture device 1000 may communicate with computing platform 1010 by way of an Internet connection via network 1015, for example. Although the computing platform of FIG. 11 shows the above-identified components, claimed subject matter is not limited to computing platforms having only these components as other implementations may include alternative arrangements that may comprise additional components, fewer components, or components that function differently while achieving similar results. Rather, examples are provided merely as illustrations. It is not intended that claimed subject matter to limited in scope to illustrative examples.

Processor 1050 may be representative of one or more circuits, such as digital circuits, to perform at least a portion of a computing procedure or process. By way of example but not limitation, processor 1050 may comprise one or more processors, such as controllers, microprocessors, microcontrollers, application specific integrated circuits, digital signal processors, programmable logic devices, field programmable gate arrays, and the like, or any combination thereof. In implementations, processing unit 1050 may perform signal processing to manipulate signals or states or to construct signals or states, for example.

Memory 1070 may be representative of any storage mechanism. Memory 1070 may comprise, for example, primary memory 1074 and secondary memory 1076, additional memory circuits, mechanisms, or combinations thereof may be used. Memory 1070 may comprise, for example, random access memory, read only memory, or one or more data storage devices or systems, such as, for example, a disk drive, an optical disc drive, a tape drive, a solid-state memory drive, just to name a few examples. Memory 1070 may be utilized to store a program, as an example. Memory 1070 may also comprise a memory controller for accessing computer readable-medium 1080 that may carry and/or make accessible content, code, and/or instructions, for example, executable by processing unit 1050 or some other controller or processor capable of executing instructions, for example.

Under the direction of processing unit 1050, memory, such as cells storing physical states, representing for example, a program, may be executed by processing unit 1050 and generated signals may be transmitted via the Internet, for example. Processing unit 1050 may also receive digitally-encoded signals from server image capture device 1000.

Network 1015 may comprise one or more communication links, processes, and/or resources to support exchanging communication signals between a client and server, which may, for example, comprise one or more servers (not shown). By way of example, but not limitation, network 1015 may comprise wireless and/or wired communication links, telephone or telecommunications systems, Wi-Fi networks, Wi-MAX networks, the Internet, the web, a local area network (LAN), a wide area network (WAN), or any combination thereof.

The term "computing platform," as used herein, refers to a system and/or a device, such as a computing device, that includes a capability to process and/or store data in the form of signals and/or states. Thus, a computing platform, in this context, may comprise hardware, software, firmware, or any combination thereof (other than software per se). Computing platform 1010, as depicted in FIG. 11, is merely one such example, and the scope of claimed subject matter is not limited to this particular example. For one or more embodiments, a computing platform may comprise any of a wide range of digital electronic devices, including, but not limited to, personal desktop or notebook computers, high-definition televisions, digital versatile disc (DVD) players and/or recorders, game consoles, satellite television receivers, cellular telephones, personal digital assistants, mobile audio and/or video playback and/or recording devices, or any combination of the above. Further, unless specifically stated otherwise, a process as described herein, with reference to flow diagrams and/or otherwise, may also be executed and/or affected, in whole or in part, by a computing platform.

Memory 1070 may store cookies relating to one or more users and may comprise a computer-readable medium that may carry and/or make accessible content, code and/or instructions, for example, executable by processing unit 1050 or some other controller or processor capable of executing instructions, for example. A user may make use of an input device, such as a computer mouse, stylus, track ball, keyboard, or any other device capable of receiving an input from a user.

Regarding aspects related to a communications or computing network, a wireless network may couple client devices with a network. A wireless network may employ stand-alone ad-hoc networks, mesh networks, Wireless LAN (WLAN) networks, cellular networks, or the like. A wireless network may further include a system of terminals, gateways, routers, or the like coupled by wireless radio links, and/or the like, which may move freely, randomly or organize themselves arbitrarily, such that network topology may change, at times even rapidly. Wireless network may further employ a plurality of network access technologies, including Long Term Evolution (LTE), WLAN, Wireless Router (WR) mesh, or 2nd, 3rd, or 4th generation (2G, 3G, or 4G) cellular technology, or other technologies, or the like. Network access technologies may enable wide area coverage for devices, such as client devices with varying degrees of mobility, for example.

A network may enable radio frequency or wireless type communications via a network access technology, such as Global System for Mobile communication (GSM), Universal Mobile Telecommunications System (UMTS), General Packet Radio Services (GPRS), Enhanced Data GSM Environment (EDGE), 3GPP Long Term Evolution (LTE), LTE Advanced, Wideband Code Division Multiple Access (WCDMA), Bluetooth, 802.11b/g/n, or other, or the like. A wireless network may include virtually any type of now known, or to be developed, wireless communication mechanism by which signals may be communicated between devices, such as a client device or a computing device, between or within a network, or the like.

Communications between a computing device and a wireless network may be in accordance with known, or to be developed cellular telephone communication network protocols including, for example, global system for mobile communications (GSM), enhanced data rate for GSM evolution (EDGE), and worldwide interoperability for microwave access (WiMAX). A computing device may also have a subscriber identity module (SIM) card, which, for example, may comprise a detachable smart card that stores subscription information of a user, and may also store a contact list of the user. A user may own the computing device or may otherwise be its primary user, for example. A computing device may be assigned an address by a wireless or wired telephony network operator, or an Internet Service Provider (ISP). For example, an address may comprise a domestic or international telephone number, an Internet Protocol (IP) address, and/or one or more other identifiers. In other embodiments, a communication network may be embodied as a wired network, wireless network, or combination thereof.

A computing device may vary in terms of capabilities or features. Claimed subject matter is intended to cover a wide range of potential variations. For example, a network device may include a numeric keypad or other display of limited functionality, such as a monochrome liquid crystal display (LCD) for displaying text. In contrast, however, as another example, a web-enabled computing device may include a physical or a virtual keyboard, mass storage, one or more accelerometers, one or more gyroscopes, global positioning system (GPS) or other location-identifying type capability, and/or a display with a higher degree of functionality, such as a touch-sensitive color 2D or 3D display, for example.

A computing device may include or may execute a variety of now known, or to be developed operating systems, or derivatives and/or versions, including personal computer operating systems, such as a Windows, iOS or Linux, or a mobile operating system, such as iOS, Android, or Windows Mobile, or the like. A computing device may include or may execute a variety of possible applications, such as a client software application enabling communication with other devices, such as communicating one or more messages, such as via email, short message service (SMS), or multimedia message service (MMS), including via a network, such as a social network including, but not limited to, Facebook, LinkedIn, Twitter, Flickr, or Google+, to provide only a few examples. A computing device may also include or execute a software application to communicate content, such as, for example, textual content, multimedia content, or the like. A computing device may also include or execute a software application to perform a variety of possible tasks, such as browsing, searching, playing various forms of content, including locally stored or streamed video, or games. The foregoing is provided merely to illustrate that claimed subject matter is intended to include a wide range of possible features or capabilities.

A network including a computing device, for example, may also be extended to another device communicating as part of another network, such as via a virtual private network (VPN). To support a VPN, transmissions may be forwarded to the VPN device. For example, a software tunnel may be created. Tunneled traffic may, or may not be encrypted, and a tunneling protocol may be substantially complaint with or substantially compatible with any past, present or future versions of any of the following protocols: IPSec, Transport Layer Security, Datagram Transport Layer Security, Microsoft Point-to-Point Encryption, Microsoft's Secure Socket Tunneling Protocol, Multipath Virtual Private Network, Secure Shell VPN, or another existing protocol, or another protocol that may be developed.

A network may be compatible with now known, or to be developed, past, present, or future versions of any, but not limited to the following network protocol stacks: ARCNET, AppleTalk, ATM, Bluetooth, DECnet, Ethernet, FDDI, Frame Relay, HIPPI, IEEE 1394, IEEE 802.11, IEEE-488, Internet Protocol Suite, IPX, Myrinet, OSI Protocol Suite, QsNet, RS-232, SPX, System Network Architecture, Token Ring, USB, or X.25. A network may employ, for example, TCP/IP, UDP, DECnet, NetBEUI, IPX, Appletalk, other, or the like. Versions of the Internet Protocol (IP) may include IPv4, IPv6, other, and/or the like.

It will, of course, be understood that, although particular embodiments will be described, claimed subject matter is not limited in scope to a particular embodiment or implementation. For example, one embodiment may be in hardware, such as implemented to operate on a device or combination of devices, for example, whereas another embodiment may be in software. Likewise, an embodiment may be implemented in firmware, or as any combination of hardware, software, and/or firmware, for example (other than software per se). Likewise, although claimed subject matter is not limited in scope in this respect, one embodiment may comprise one or more articles, such as a storage medium or storage media. Storage media, such as, one or more CD-ROMs and/or disks, for example, may have stored thereon instructions, executable by a system, such as a computer system, computing platform, or other system, for example, that may result in an embodiment of a method in accordance with claimed subject matter being executed, such as a previously described embodiment, for example; although, of course, claimed subject matter is not limited to previously described embodiments. As one potential example, a computing platform may include one or more processing units or processors, one or more devices capable of inputting/outputting, such as a display, a keyboard and/or a mouse, and/or one or more memories, such as static random access memory, dynamic random access memory, flash memory, and/or a hard drive.

In the preceding detailed description, numerous specific details have been set forth to provide a thorough understanding of claimed subject matter. However, it will be understood by those skilled in the art that claimed subject matter may be practiced without these specific details. In other instances, methods and/or apparatuses that would be known by one of ordinary skill have not been described in detail so as not to obscure claimed subject matter. Some portions of the preceding detailed description have been presented in terms of logic, algorithms, and/or symbolic representations of operations on binary signals or states, such as stored within a memory of a specific apparatus or special purpose computing device or platform. In the context of this particular specification, the term specific apparatus or the like includes a general purpose computing device, such as general purpose computer, once it is programmed to perform particular functions pursuant to instructions from program software.

Algorithmic descriptions and/or symbolic representations are examples of techniques used by those of ordinary skill in the signal processing and/or related arts to convey the substance of their work to others skilled in the art. An algorithm is here, and generally, is considered to be a self-consistent sequence of operations and/or similar signal processing leading to a desired result. In this context, operations and/or processing involves physical manipulation of physical quantities. Typically, although not necessarily, such quantities may take the form of electrical and/or magnetic signals and/or states capable of being stored, transferred, combined, compared, processed or otherwise manipulated as electronic signals and/or states representing information. It has proven convenient at times, principally for reasons of common usage, to refer to such signals and/or states as bits, data, values, elements, symbols, characters, terms, numbers, numerals, information, and/or the like. It should be understood, however, that all of these or similar terms are to be associated with appropriate physical quantities and are merely convenient labels. Unless specifically stated otherwise, as apparent from the following discussion, it is appreciated that throughout this specification discussions utilizing terms such as "processing," "computing," "calculating," "determining", "establishing", "obtaining", "identifying", "selecting", "generating", and/or the like may refer to actions and/or processes of a specific apparatus, such as a special purpose computer and/or a similar special purpose computing device. In the context of this specification, therefore, a special purpose computer and/or a similar special purpose computing device is capable of processing, manipulating and/or transforming signals and/or states, typically represented as physical electronic and/or magnetic quantities within memories, registers, and/or other information storage devices, transmission devices, and/or display devices of the special purpose computer and/or similar special purpose computing device. In the context of this particular patent application, as mentioned, the term "specific apparatus" may include a general purpose computing device, such as a general purpose computer, once it is programmed to perform particular functions pursuant to instructions from program software.

In some circumstances, operation of a memory device, such as a change in state from a binary one to a binary zero or vice-versa, for example, may comprise a transformation, such as a physical transformation. With particular types of memory devices, such a physical transformation may comprise a physical transformation of an article to a different state or thing. For example, but without limitation, for some types of memory devices, a change in state may involve an accumulation and/or storage of charge or a release of stored charge. Likewise, in other memory devices, a change of state may comprise a physical change, such as a transformation in magnetic orientation and/or a physical change or transformation in molecular structure, such as from crystalline to amorphous or vice-versa. In still other memory devices, a change in physical state may involve quantum mechanical phenomena, such as, superposition, entanglement, and/or the like, which may involve quantum bits (qubits), for example. The foregoing is not intended to be an exhaustive list of all examples in which a change in state form a binary one to a binary zero or vice-versa in a memory device may comprise a transformation, such as a physical transformation. Rather, the foregoing is intended as illustrative examples.

While there has been illustrated and/or described what are presently considered to be example features, it will be understood by those skilled in the relevant art that various other modifications may be made and/or equivalents may be substituted, without departing from claimed subject matter. Additionally, many modifications may be made to adapt a particular situation to the teachings of claimed subject matter without departing from one or more central concept(s) described herein. Therefore, it is intended that claimed subject matter not be limited to the particular examples disclosed, but that such claimed subject matter may also include all aspects falling within appended claims and/or equivalents thereof.

What is claimed is:

1. An apparatus, comprising:
   at least one processor coupled to at least one memory, the at least one processor coupled to the at least one memory being programmed to:
   process optical spectra comprising optical measurements of at least one portion of an illuminated object at a plurality of focal positions between the object and an imaging lens and at a plurality of angular orientations to be relative to a substantially transverse directional path of light to illuminate the object, wherein the optical measurements are to result from transmission of one or more optical signals along the substantially transverse directional path;

rotate, in a plane representations of the processed optical measurements; and project the rotated representations of the processed optical measurements onto a coordinate plane in a manner so that in-focus and out-of-focus rotated representations of the processed optical measurements are to form a cross-sectional image of the at least one portion.

2. The apparatus of claim 1, wherein the at least one processor coupled to the at least one memory being further programmed to project the rotated representations of the processed optical measurements onto a coordinate plane in order additionally to combine the processed optical measurements via at least partial superposition onto the coordinate plane.

3. The apparatus of claim 2, wherein the at least one processor coupled to the at least one memory that is programmed to combine the processed optical measurements via at least partial superposition onto the coordinate plane, being further programmed to perform linear transformations.

4. The apparatus of claim 1, wherein the illuminated object to comprise a phase object and wherein the at least one processor coupled to the at least one memory being further programmed to process optical measurements of at least one portion of the illuminated phase object.

5. The apparatus of claim 4, wherein the illuminated phase object to comprise a biological tissue; and wherein the at least one processor coupled to the at least one memory being further programmed to process optical measurements of at least one portion of the illuminated biological tissue.

6. The apparatus of claim 4, wherein the illuminated phase object to comprise at least one optical fiber; and wherein the at least one processor coupled to the at least one memory being further programmed to process optical measurements to process optical measurements of at least one portion of the illuminated at least one optical fiber.

7. The apparatus of claim 1, wherein the illuminated object is to comprise at least one optical fiber; and wherein the at least one processor coupled to the at least one memory being further programmed to process optical measurements of a cross-sectional area of at least one optical fiber, the at least one optical fiber to include at least one dopant to produce spontaneous optical emission in response to optical pumping.

8. The apparatus of claim 7, wherein the at least one optical fiber comprises a region of spontaneous optical emission; and wherein the at least one processor coupled to the at least one memory being further programmed to process optical measurements of at least a cross-sectional area of a region the spontaneous optical emission.

9. The apparatus of claim 7, wherein the at least one optical fiber to produce amplified spontaneous emission; and wherein at least one processor coupled to the at least one memory being further programmed to process optical measurements of the at least one cross-sectional area.

10. The apparatus of claim 1, wherein the illuminated object is capable of attenuation of optical energy for a range of spectra; and wherein the at least one processor coupled to the at least one memory being further programmed to process optical measurements of a region of the illuminated object capable of attenuation of optical energy for a range of spectra, wherein the at least one processor coupled to the at least one memory also being further programmed to process optical measurements of the at least one portion of the illuminated object comprising a cross-sectional area of the region of the illuminated object capable of attenuation of optical energy for a range of spectra, and wherein the at least one processor coupled to the at least one memory also being further programmed to process optical measurements responsive to one or more optical signals to produce measurable optical characteristics at least within the range of the spectra.

11. The apparatus of claim 1, wherein the at least one processor coupled to the at least one memory being further programmed to:

filter at least some of the in-focus and the out-of-focus representations.

12. The apparatus of claim 11, wherein the at least one processor coupled to the at least one memory being further programmed to filter at least some of the in-focus and the out-of-focus representations substantially in accordance with at least one of the following: a Ram-Lak filter, a Shepp-Logan filter, a Hamming filter, a cosine filter, or any combination thereof.

13. An apparatus having a non-transitory storage medium and a controller thereof, the non-transitory storage medium comprising:

a non-transitory storage medium including executable instructions stored thereon;

wherein the instructions are executable by at least one processor coupled to at least one memory, to:

process optical spectra comprising optical measurements of at least one portion of an illuminated object at a plurality of focal positions between the object and an imaging lens and at a plurality of angular orientations to be relative to a substantially transverse directional path of light to illuminate the object, wherein the optical measurements are to result from transmission of one or more optical signals along the substantially transverse directional path;

rotate, in a plane, representations of the processed optical measurements; and project the rotated representations of the processed optical measurements onto a coordinate plane in a manner so that in-focus and out-of-focus rotated representations of the processed optical measurements are to form a cross-sectional image of the at least one portion.

14. The apparatus of claim 13, wherein the executable instructions to project the rotated representations of the processed optical measurements onto a coordinate plane are further to combine and process optical measurements via at least partial superposition onto the coordinate plane.

15. The apparatus of claim 14, wherein the executable instructions to process optical measurements via at least partial superposition are further to perform linear transformations.

16. The apparatus of claim 13, wherein the illuminated object to comprise a phase object; and wherein the executable instructions are further to process optical measurements of at least one portion of the illuminated phase object.

17. The apparatus of claim 16, wherein the illuminated phase object to comprise biological tissue; and wherein the executable instructions are to process optical measurements of at least one portion of the illuminated biological tissue.

18. The apparatus of claim 16, wherein the illuminated phase object to comprise at least one optical fiber; and wherein the executable instructions are to process optical measurements of at least one portion of the at least one optical fiber.

19. The apparatus of claim 18, wherein the at least one optical fiber to comprise at least one dopant to produce spontaneous optical omission in response to optical pumping, and wherein the executable instructions to process optical measurements of the at least one portion of the illuminated object are further to process measurements of a cross-sectional area of the at least one optical fiber.

20. The apparatus of claim 19, wherein the at least one optical fiber to generate spontaneous optical omission, and wherein the executable instructions are further to process optical measurements of the spontaneous optical emission from the at least one portion of the cross-sectional area of the at least one optical fiber.

21. The apparatus of claim 19, wherein the at least one optical fiber to produce amplified spontaneous emission, and wherein the executable instructions are further to process optical measurements of the amplified spontaneous emission.

22. The apparatus of claim 13, wherein the at least one portion of the illuminated object is capable of attenuating optical energy for a range of spectra and wherein the instructions are executable by at least one processor coupled to the at least one memory to:
  process optical measurements of a cross-sectional area of the illuminated object, and
  process optical measurements of optical characteristics at least within the range of the spectra responsive to one or more optical signals.

23. The apparatus of claim 13, wherein the executable instructions are further to filter at least some of the in-focus and the out-of-focus representations.

24. The apparatus of claim 23, wherein the executable instructions are further to filter at least some of the in-focus and the out-of-focus representations substantially in accordance with at least one of the following: a Ram-Lak filter, a Shepp-Logan filter, a Hamming filter, a cosine filter, or any combination thereof.

* * * * *